United States Patent [19]

Sellstedt

[11] 4,008,226
[45] Feb. 15, 1977

[54] INTERMEDIATES FOR PREPARING SEMI-SYNTHETIC CEPHALOSPORINS AND PROCESSES RELATING THERETO

[75] Inventor: John H. Sellstedt, King of Prussia, Pa.

[73] Assignee: American Home Products Corporation, New York, N.Y.

[22] Filed: July 28, 1975

[21] Appl. No.: 599,565

Related U.S. Application Data

[60] Division of Ser. No. 217,942, Jan. 14, 1972, Pat. No. 3,962, 215, which is a continuation-in-part of Ser. No. 186,397, Oct. 4, 1971, Pat. No. 3,896,110.

[52] U.S. Cl. .......................... 260/243 C; 424/246; 260/239.1; 424/271
[51] Int. Cl.² ....................................... C07D 501/18
[58] Field of Search ................................ 260/243 C

[56] References Cited

UNITED STATES PATENTS 3,853,860  12/1974  Weir ............................... 260/243 C Primary Examiner—Nicholas S. Rizzo

[57] ABSTRACT

Phosphorylated penicillins and cephalsporins are described which are obtained by reacting a penicillin or cephalosporin with a trivalent or pentavalent phosphorus halide and treating the thus formed product sequently with an acid chloride, an alcohol and water to form a phosphorylated anhydride of a 6-aminopenicillanic acid or 7-aminocephalosporanic acid salt, respectively, and thereafter acylating the thus formed product and splitting off the carboxyl protective group to obtain the desired penicillin or cephalosporin compound.

14 Claims, No Drawings

INTERMEDIATES FOR PREPARING SEMI-SYNTHETIC CEPHALOSPORINS AND PROCESSES RELATING THERETO

This application is a continuation-in-part of copending application Ser. No. 186,397 now Pat. No. 3,896,110 issued July 22, 1975 filed Oct. 4, 1971 and a division of copending application Ser. No. 217,942 filed January 14, 1972, U.S. Pat. No. 3,962,215 June 8, 1976.

This invention relates to novel phosphorylated penicillin and cephalosporin derivatives and processes relating to their preparation and use in manufacturing semi-synthetic penicillins and cephalosporins.

In its broadest aspects the present invention covers compounds containing the following chemical structure:

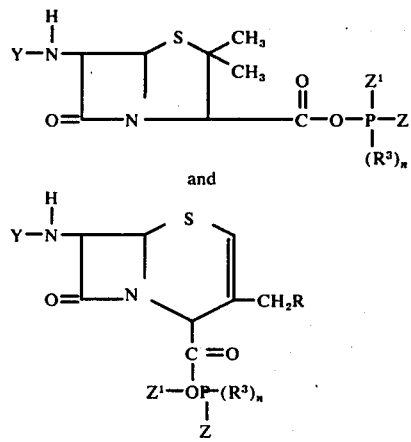

and

Z and Z' are each an organic radical and may be joined together to form a heterocyclic ring with the phosphorous atom; Y is hydrogen or an acyl radical. These compounds are useful as intermediates to product non-toxic cephalosporins and penicillins exhibiting gram positive and/or gram negative activity against microorganisms. In its more narrow aspects the invention provides compounds of the formulae

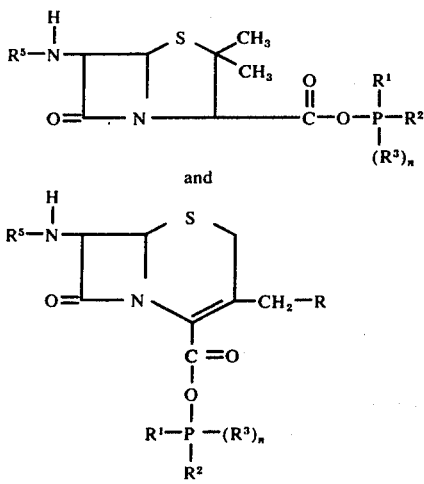

wherein:
R is selected from the class consisting of hydrogen, (lower) alkanoyloxy containing 2 to 8 carbon atoms (e.g. acetoxy), propionoyloxy, and A' butanoyloxy etc.), aryloxy, a quaternary ammonium radical (e.g. pyridinium, quinolinium, picolinium, etc.); $R^3$ is oxygen (=O) when the phosphorus atom is pentavalent; $R^5$ is selected from the class consisting of hydrogen and an organic acyl group; $R^1$ and $R^2$ are selected from the class consisting of (lower)alkoxy, (lower)alkylthio, aryloxy, arylthio, aryl(lower)alkyloxy, aryl (lower)alkylthio, halogen, (lower)alkyl, aryl, aryl(lower)alkyl, halo(lower)alkyloxy, halo(lower)alkyl and a radical of the following structure:

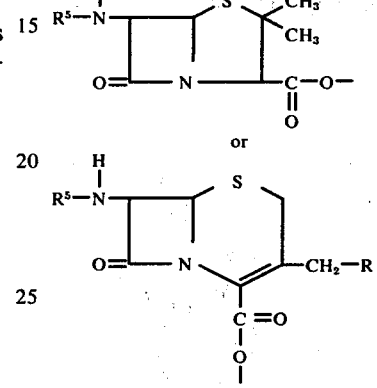

Preferably, $R^1$ and $R^2$ are joined together to form with the phosphorus atom the ring:

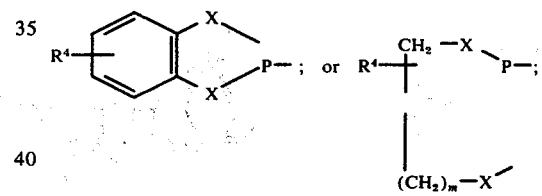

$n$ is an integer from 0 to 1; $m$ is an interger from 1 to 6; X is selected from the class consisting of sulfur; oxygen methylene $R^4$ is selected from the class consisting of hydrogen and from one to three (lower)alkyl radicals; X is preferably oxygen.

The term "(lower)alkyl" as employed herein alone or in conjunction with other designated groups is intended to encompass straight chain or branch chain alkyl groups consisting of from one through six carbon atoms (e.g. methyl, ethyl, propyl, butyl, isobutyl, hexyl, 2-ethylpropyl, etc.).

The term "(lower)alkoxy" as employed herein alone or in conjunction with other designated groups is intended to encompass straight chain or branched chain alkoxy groups having one through six carbon atoms (e.g. methoxy, propoxy, butoxy, isobutoxy, pentoxy, 1,1-dimethylbutoxy). The term "halogen" as used herein is intended to encompass chlorine, bromine, iodine and fluorine. The term "aryloxy" encompasses phenoxy, naphthoxy, as well as unsaturated heterocyclic rings containing 5 to 7 ring members and from 1 to 3 hetero atoms selected from the class consisting of nitrogen, oxygen and sulfur. The term "aryl(lower)alkyloxy" encompasses an aryl nucleus linked through a ring carbon atom to a (lower)alkyloxy group. Illustrative of aryl(lower)alkyloxy) are benzyloxy, phenethyloxy, etc. The term "aryl" is illustrated by phenyl and naphthyl and the term "aryl(lower)alkyl" is illustrated by benzyl, phenethyl, etc. Illustrative of (lower-)alkylthio are thiomethyl, thiobutyl, thioisopropyl, etc. Illustrative of "arylthio" are phenylthio, chlorophenylthio, methylphenylthio, methoxyphenylthio, etc. Illustrative of "aryl(lower)alkylthio" are benzylthio, phenethylthio, chlorophenethylthio, etc.

The acyl group defined by $R^5$ is derived from an organic carboxylic acid or organic sulfonic acid or a suitable reactive functional derivative thereof.

The preferred acyl groups defined by $R^5$ are selected from groups having the following formulae wherein those having a free amino group are in the form of an acid addition salt which may subsequently be converted to the free base.

$R^6$ and $R^7$ are selected from the group consisting of hydrogen and (lower)alkoxy;

$R^8$ is selected from the group consisting of hydrogen, (lower)alkyl and phenyl;

$R^9$ and $R^{10}$ are selected from the group consisting of hydrogen and halogen;

$R^{11}$ and $R^{12}$ are selected from the group consisting of hydrogen, halogen, (lower)alkyl, (lower)alkoxy, phenyl and phenoxy;

$R^{13}$ is selected from the class consisting of hydrogen, (lower)alkyl and aryl;

$a$ is an interger from 0 to 1; $b$ is an interger from 0 through 5; ;

$c$ is an interger from 0 to 2; $d$ is an interger from 1 through 3, with the proviso that when $a$ is 0, $d$ is greater than 1, and when $a$ is 1, $d$ is less than 3.

The process of the present invention is illustrated by the following flow diagram:

wherein:

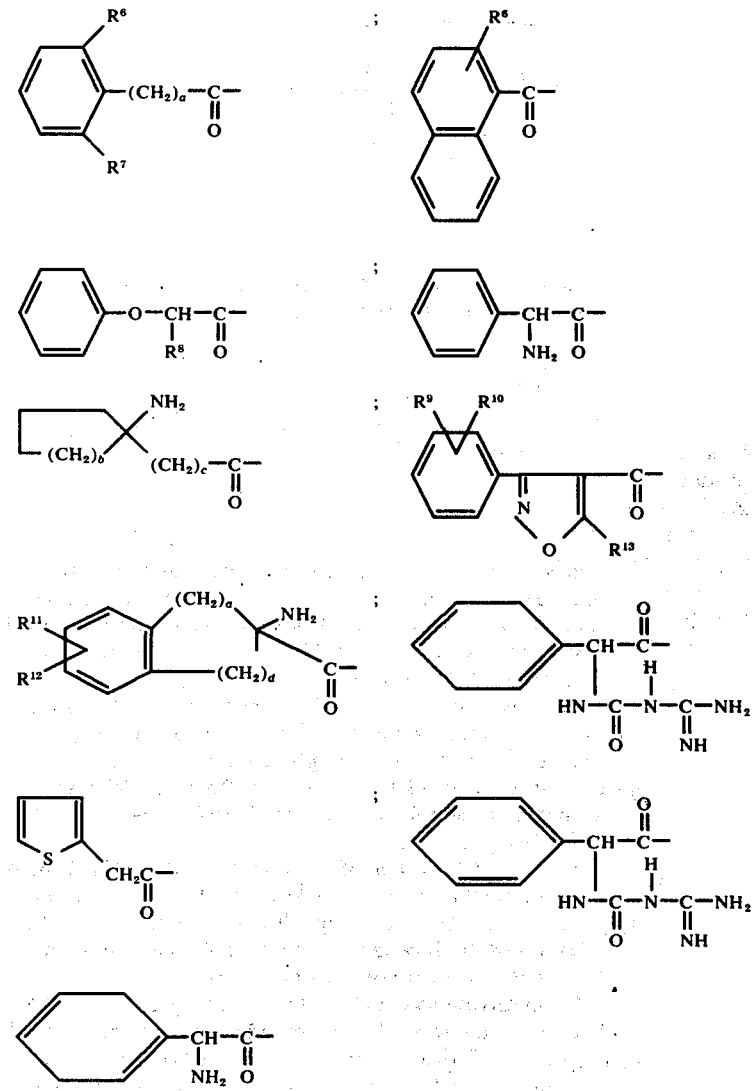

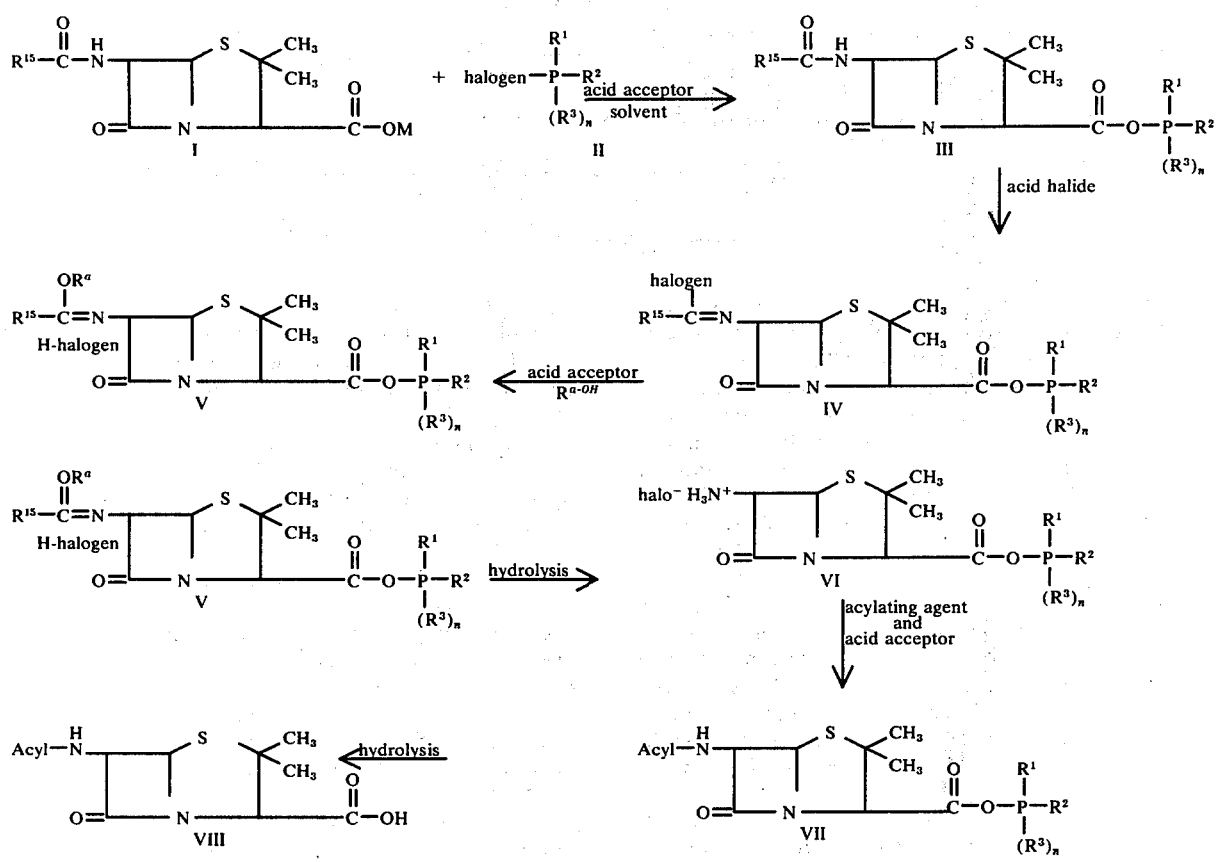

In the foregoing reaction sequence M is selected from the class consisting of hydrogen, alkali metal (e.g. Na, K. etc.) and a tertiary amine (e.g. triethylamine, dimethylaniline) and $R^{15}$ is a substituent selected from those contained in natural and synthetic penicillins. As used herein the term "natural penicillins" include those which are produced by fermentation as well as those that are biosynthetically prepared by the addition of certain precursors to the fermentation broth. Examples of these penicillins are: Penicillin S ($R^{15}$ is -chlorocrotylmercaptomethyl); Penicillin V ($R^{15}$ is phenoxymethyl); Penicillin G ($R^{15}$ is benzyl); Penicillin F ($R^{15}$ is 2-pentyl); Penicillin K ($R^{15}$ is 2-heptyl); Penicillin X ($R^{15}$ is P-hydroxybenzyl); Dihydro Penicillin F ($R^{15}$ is amyl); Penicillin T ($R^{15}$ is p-aminobenzyl); Penicillin O ($R^{15}$ is allylmercaptomethyl); Penicillin N ($R^{15}$ is 4-amino-4-carboxybutyl). Although it is preferred to use a natural penicillin as the starting material of formula I for reaction with a phosphorus halide of formula II, the process is not limited in operability to these starting materials and will operate utilizing a synthetic penicillin as a reactant within the scope of the formula I.

Illustrative of specific phosphorus halides falling within the scope of formula II are phosphorus oxychloride, phosphorus trichloride, diphenyl phosphorochloridate, phosphorochloridate, phenyl phosphorodichloridate, ethyl phosphorodichloridate, cyclic ethylene phosphorochloridate, diethyl phosphorochloridate, diethyl phosphorochloridite, ethyl phosphorodichloridite, cyclic ethylene phosphorochloridite (2-chloro-1,3,2-dioxaphospholane), cyclic propylene phosphorochloridite (2-chloro-1,3,2-dioxaphosphorinane), etc.

The reaction of a compound of formula I with a compound of formula II is preferably carried out in the presence of an anhydrous inert aprotic solvent and acid binding agent. This reaction is carried out at a temperature in the range of about −40° to about +10° C., preferably −10° C. to about +10° C. The molar ratio of a compound of formula I to a compound of formula II is about 0.5:1 to 3:1, preferably about 1:1. Where the molar ratio is greater than 1:1 and at least one of $R^1$ or $R^2$ is halogen, dimers or trimers can be obtained as illustrated by the following formulae:

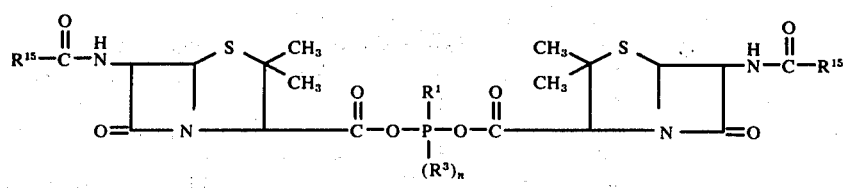

and

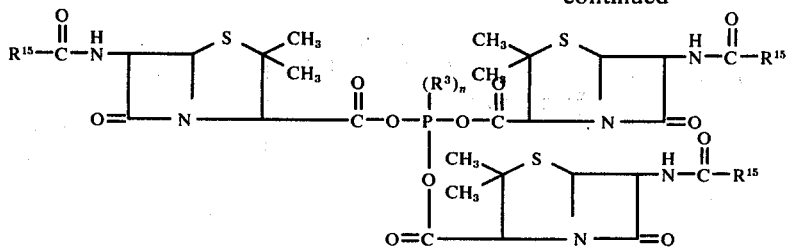

Suitable acid binding agents are tertiary amines such as triethyl amine, dimethylaniline, quinoline, pyridine, lutidine, alkali metal carbonates; alkaline earth carbonates or other acid binding agents known in the art. The preferred acid binding agent is a weak tertiary amine. As used herein "strong amines" are those characterized by having dissociation constants in the range of from $10^{-3}$ to $10^{-6}$ or having comparable basicity, as distinguished from "weak amines" which are characterized by having dissociation constants in the range of from $10^{-8}$ to $10^{-11}$.

A wide range of anhydrous non-hydroxylic organic solvents are useful in the reaction of a compound of formula I with a phosphorylating agent including hydrocarbons such as toluene; chlorinated solvents such as methylene chloride, chloroform and chlorobenzene; ethers such as diethyl ether, tetrahydrofuran; and other conventional solvents such as methylisobutylketone, dimethylformamide, ethyl acetate, acetonitrile, etc., the preferred solvents being the chlorinated solvents.

The carboxy protected penicillin represented by formula III is converted to the corresponding imino halide represented by formula IV by reaction with an acid chloride in the presence of an acid acceptor. Examples of suitable acid halides includes phosphorus pentachloride, phosgene, phosphorus oxychloride, oxalyl A' chloride, p-toluene sulfonic acid chloride, phosphorus pentabromide, etc. The acid acceptor is an acid binding agent which may be any one of those previously described in connection with the reaction of a compound of formula I with a compound of formula II. The formation of the imino halide compound is carried out under anhydrous conditions at temperatures below 0° C., preferably between −10° C. and −65° C. An inert organic solvent such as methylene chloride, dichloroethane, chloroform, diethyl ether, or any other solvent previously described herein is present during the reaction. Since it is not necessary to isolate the intermediate of formula III (although this may be done), the solvent used in reacting a compound of formula I with a compound of formula II is present when a compound of formula III is reacted with an acid halide. A slight excess of acid halide, not more than about 10%, is used in the formation of a compound of formula IV.

The imino compound of formula IV is converted to the imino ether hydrohalide of formula V by reacting the imino halide under anhydrous conditions with a primary or secondary alcohol ($R^aOH$) at temperatures below about −10° C., preferably between about −30° C. and −60° C. At these temperatures, the carboxyl protecting group is resistant to splitting off. Illustrative of $R^a$ is lower alkyl, hydroxy(lower)alkyl, phenyl(lower)alkyl, cycloalkyl of 4 to 8 carbon atoms, (lower)alkoxy(lower)alkyl, aryloxy(lower)alkyl, etc.

Examples of suitable primary and secondary $R^aOH$ compounds are methanol, ethanol, n-butanol, isopropanol, amyl alcohol, benzyl alcohol, 2-phenylethanol-1, cyclohexyl alcohol, 1,6 hexanediol, 2-methoxyethanol, 2-isopropoxyethanol, 2-butoxyethanol, 2-p-chlorophenoxyethanol, 2-(p-methoxybenzyloxy)-ethanol, diglycol, etc.

The imino ether bond is split without removal of the carboxyl protecting group. This is accomplished by hydrolysis with water at a temperature below −20° C., preferably the temperature is between −30° C. and −60° C.

After formation of a compound of formula VI, acylation is carried out at a temperature between −60° C. and room temperature, preferably below 0° C. in the presence of an acid binding agent which may be one of materials previously described, to produce a compound of formula VII. The acid binding agent is preferably a weak amine. Sufficient acid binding agent must be employed to remove the hydrogen halide from a compound of formula VI, and permit immediate acylation of the 6-amino group. In carrying out this reaction an excess of acylating agent to acid acceptor is employed.

Suitable acylating agents include carboxylic acid halides, carboxylic acid anhydrides, mixed anhydrides with other carboxylic or inorganic acids; esters such as thiol esters and phenol esters; lactones; and carboxylic acids with carbodiimides or N,N¹-carboxyldiimidazoles.

Illustrative of some specific preferred acylating agents are phenoxyacetyl chloride, 2,6-dimethoxybenzoyl chloride, benzene sulfonyl chloride, 2-phenoxypropionyl chloride, 2-phenoxybutryl chloride, D(−)phenylglycyl chloride HCl, 1-aminocyclopentanecarboxylic acid chloride HCl, 1-aminocyclohexanecarboxylic acid chloride HCl, 2-amino-2-carboxyindane acid chloride HCl, 2-ethoxy naphthoyl bromide and 3-(2,6-dichlorophenyl)-5-methyl-isoxazole-4-carbonyl chloride, etc.

The acylated penicillin of formula VII is obtained as the hydrohalide salt if the acyl radical contains an α or β-amino group. This intermediate of formula VII is converted to a semi-synthetic penicillin compound of formula VIII by hydrolysis to remove the carboxyl protecting group. If this product is in the form of a hydrohalide salt, it is readily converted to its corresponding basic form by neutralization processes which are well known to those skilled in the art of chemistry. For example, the hydrohalide salt is treated for a short time with water containing a base, such as triethylamine, sodium bicarbonate or the like, preferably in the presence of a water-miscible solvent.

In the event the ultimate penicillin to be obtained is α-aminobenzyl penicillin (ampicillin), it has been found advantageous to change the halide to an aryl sulfonic acid salt of the aminopenicillin either by adding an appropriate sulfonic acid to the reaction mixture comprising the selected organic solvent and water, or to the aqueous extracts separated as described immediately above. In this connection, a 25% excess of the sulfonic acid has been used to advantage in preparing the corresponding salt of ampicillin.

The aryl sulfonic salt of the α-aminobenzyl penicillin may then be converted to the penicillin per se by reaction with a base such as triethylamine or diethylamine in approximately 85% isopropanol. In the case of ampicillin specifically, the sulfonic acid salt, wet with water and ethyl acetate, may be added to isopropanol containing a molar equivalent of triethylamine at 75°–80° C., whereby the anhydrous form of ampicillin described and claimed in U.S. Pat. No. 3,144,445 is formed and collected by filtration from the hot mixture.

Alternatively, the corresponding penicillin may be obtained, but in hydrated form, by raising the pH of the aqueous reaction mixture containing the hydrochloride salt of said penicillin to the iso-electric point.

In place of a penicillin of formula I, a cephalosporin of the following formula can be used to produce semisynthetic cephalosporins

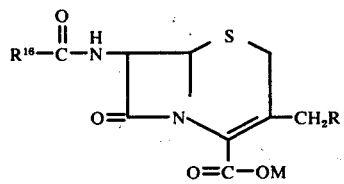

wherein R and M have the same meaning as previously defined and $R^{16}$ is a substituent selected from those contained in natural and synthetic cephalosporins as exemplified by the numerous examples in the prior art. Illustrative of substituents from natural cephalosporins are 2-thienylmethyl, (Cephalothin); 4-amino-4-carboxy-n-butyl, (Cephalothin C); other cephalosporin compounds are illustrated by those disclosed in U.S. Pat. Nos. 3,499,909; 3,093,638; 3,207,755.

The natural or synthetic penicillins and cephalosporins employed as starting materials are commercially available or are described in the literature. Similarly, the phosphorus halides of formula II are commercially available or in those instances where they are not available, they may be synthesized readily by standard organic procedures described in the chemical literature and known to those skilled in the art.

The following examples are given by way of illustrating some embodiments of this invention.

EXAMPLE 1

D(—)α-aminobenzylpenicillin

Potassium penicillin G (75 g., 0.2 mole) and N,N-dimethylaniline (DMA) (53 ml., 0.418 mole) are stirred in 300 ml. of dichloromethane at 10° C. while 2-chloro-1,3,2-dioxaphospholane (27 ml., 0.3 mole) is added over 20 min. The resulting product is 6-phenylacetamido penicillanic acid, 1,3,2-dioxaphospholan-2-yl ester. After stirring an additional one-half hr. at 10° C. the temperature is lowered to —55° C. and powdered $PCl_5$ (45 g., 0.216 mole) is added all at once. With continuous cooling in an acetone-dry ice bath, the temperature rises to about —45° C., and the mixture is stirred for 2 hr. at —40° C. The product obtained from this reaction is 6-[(α-chlorophenethylidene)amino]-penicillanic acid, 1,3,2-dioxaphospholan-2-yl ester.

The temperature is again lowered to —60° C., and 67 ml. of absolute alcohol is added at the fastest rate allowable so that the temperature may be kept below —40° C. to produce 6-[(α-ethoxyphenethylidene)amino]penicillanic acid, 1,3,2-dioxaphospholan-2-yl ester. After stirring 2½ hr. at —40° C. the temperature is lowered to —50° C. and 52.5 ml. of water is dripped in without allowing the temperature to go above —40° C. to produce the hydrochloride salt of 6-aminopenicillanic acid, 1,3,2-dioxaphospholan-2-yl ester. After stirring overnight (about 18 hr.) at —40° C., the flask is equipped with a dropping funnel containing 112 ml. of dimethylaniline and a 250 ml. Erlenmeyer flask containing 52.5 g. of D-(—)-phenylglycylchloride hydrochloride connected with a Gooch tube.

About one-sixth of the acid chloride is added and dimethylaniline is slowly dropped in. At this point the temperature is allowed to rise to —25° C. The two are concurrently added so that all the acid chloride is added over 30 min. and the dimethylaniline added over 40 min., with the object being to always have more acid chloride present in the mixture than dimethylaniline. After another 40 min. the reaction mixture is almost clear, the hydrochloride salt of D(—)-α-aminophenylacetamido penicillanic acid, 1,3,2-dioxaphospholan-2-yl ester is poured into 700 ml. water, and the flask rinsed with 100 ml. water to produce the hydrochloride salt of D(—)-α-aminobenzylpenicillin. The aqueous mixture is rapidly stirred in an ice bath for 15 min. Super-Cell is added, the mixture is filtered, and the cake washed with 200 ml. water. After separation of the layers, the aqueous phase is placed in a 2 liter, 4 neck flask and 150 ml. ethylacetate added. The mixture is cooled to 0°–10° C., the pH adjusted to 1.7 with 5N sodium hydroxide, and 105 ml. of 37% naphthalene sulfonic acid is added over about 10 min. at 0°–10° C. while keeping the pH at 1.5–1.7 with 5N sodium hydroxide. During the addition of the naphthalene sulfonic acid, some seeds of the naphthalene sulfonic acid salt of D(—)-α-aminobenzylpenicillin are added and the flask is scratched to hasten crystallization. Stirring is continued for 6 hr. at 0°–10° C. and the naphthalene sulfonic acid salt of D(—)-α-aminobenzylpenicillin is filtered off. It is stirred in 250 ml. of cold, pH 1.5 to 1.7 water for 5 min. and filtered. The cake is pressed and sucked fairly dry, and then stirred for 5 min. in 250 ml. of ethylacetate. The slurry is filtered and the cake washed twice with ethylacetate giving 109 g. of naphthalene sulfonic acid salt of D(—)-α-aminobenzylpenicillin with a NVM of 54.5%, and a corresponding 53% yield of naphthalene sulfonic acid salt of D(—)-α-aminobenzylpenicillin. This salt is converted to anhydrous ampicillin by the standard isopropanol procedure described in U.S. Pat. No. 3,487,073.

EXAMPLE 2

α-aminobenzylpenicillin

Following the procedure of Example 1, but using 31 ml. (0.3 moles) of 2-chloro-1,3,2-dioxaphosphorinane and 45 ml. of water the naphthalene sulfonic acid salt of 6-α-aminobenzylpenicillin is isolated in 56% yield.

EXAMPLE 3

Potassium penicillin G (75 g., 0.2 moles) and N,N-dimethylaniline (DMA) (53 ml., 0.418 moles) are stirred in 300 ml. of dichloromethane at 0° C. while phosphorus trichloride (8.8 ml., 0.1 mole) is added over 10 minutes. After stirring an additional one-half hour at 0° C., the temperature is lowered to −55° C. and powdered $PCl_5$ (45 g., 0.216 mole) is added all at once. With continuous cooling in an acetone-dry ice bath, the temperature rises to about −45° C., and the mixture is stirred for 2 hours at −40° C. The temperature is again lowered to −60° C. and 72.8 ml. of absolute alcohol containing 12.7 ml. (0.1 mole) of DMA is added at the fastest rate allowable so that the temperature could be kept below −40° C. After stirring 2½ hours at −40° C. the temperature is lowered to −50° C. and 45 ml. of water is dripped in without allowing the temperature to go above −40° C. The reaction is then reacted and worked up in a manner similar to Example 1 giving the naphthalene sulfonic acid salt of 6-α-aminobenzyl penicillin in 57% yield.

The following Examples 4 through 8 are illustrative of specific carboxyl protected penicillins and cephalosporins that may be prepared in accordance with the process of the present invention.

EXAMPLE 4

Example 4

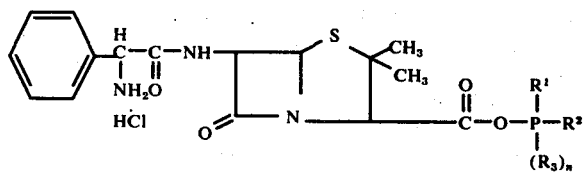

wherein $R^1$, $R^2$, $R^3$, $R^1+R^2$ and n are defind as follows:

| $R^1$ | $R^2$ | $R^3$ | $R^1+R^2$ | n |
|---|---|---|---|---|
| Cl | Cl | | =0 | 1 |
| Cl | $OCH_3$ | | | 0 |
| $OCH_3$ | $OCH_3$ | | =0 | 1 |
| O—φ | O—φ | | | 0 |
| O—$CH_2$—φ | Cl | | =0 | 1 |
| $OC_2H_5$ | $OC_2H_5$ | | | 0 |
| — | — | | 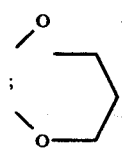 | 0 |
| — | — | | | 0 |
| O—φ | O—$CH_2$—φ | | 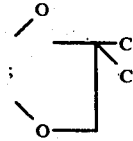 | 0 |

EXAMPLE 5

Example 5

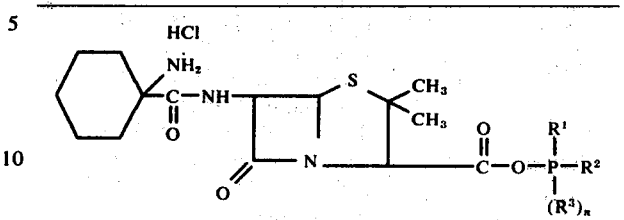

wherein $R^1$, $R^2$, $R^3$, $R^1+R^2$ and n are defined as follows:

| $R^1$ | $R^2$ | $R^3$ | $R^1+R^2$ | n |
|---|---|---|---|---|
| Br | Br | | —0 | 1 |
| Cl | $OC_2H_5$ | | | 0 |
| O—φ | Cl | | —0 | 1 |
| Cl | $OC_2H_5$ | | —0 | 1 |
| $OC_2H_5$ | $OC_2H_5$ | | | 0 |
| O—$CH_2$—φ | O—$CH_2$—φ | | | 0 |
| — | — | | | 0 |

EXAMPLE 6

Example 6

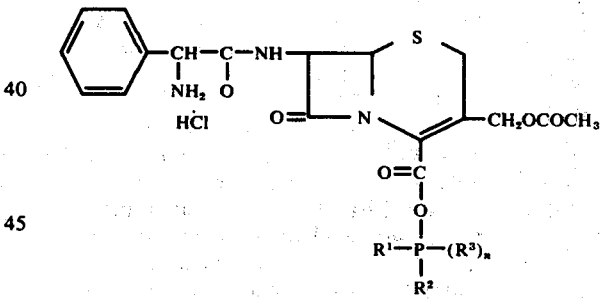

wherein $R^1$, $R^2$, $R^3$, $R^1+R^2$ and n are defined as follows:

| $R^1$ | $R^2$ | $R^3$ | $R^1+R^2$ | n |
|---|---|---|---|---|
| Cl | Cl | | =0 | 1 |
| $OC_2H_5$ | $OC_2H_5$ | | =0 | 1 |
| Cl | O—φ | | =0 | 1 |
| Cl | $OC_2H_5$ | | | 0 |
| O—$CH_2$—φ | Cl | | =0 | 1 |
| O—φ | O—φ | | | 1 |
| — | — | | | 0 |

EXAMPLE 7

Example 7

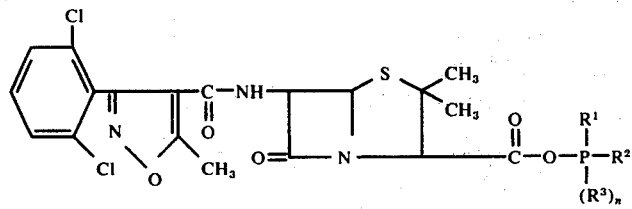

wherein R¹, R², R³, R¹+R² and n are defined as follows:

| R¹ | R² | R³ | R¹+R² | n |
|---|---|---|---|---|
| Cl | Cl | =O | | 1 |
| OCH₃ | OCH₃ | =O | | 1 |
| O—φ | OCH₃ | | | 0 |
| Cl | OC₂H₅ | =O | | 1 |
| O—CH₂—φ | O—=2—φ | | | 0 |
| O—φ | Cl | =O | | 1 |
| — | — | | 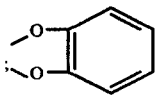 | 0 |

EXAMPLE 8
Example 8

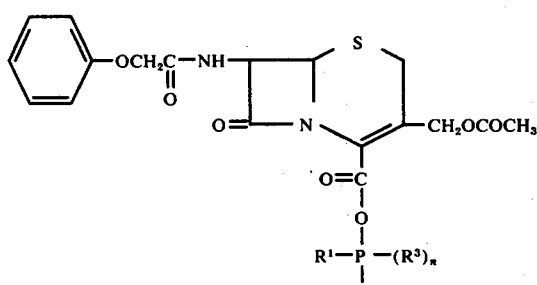

wherein R¹, R², R³, R¹+R² and n are defined as follows:

| R¹ | R² | R³ | R¹+R² | n |
|---|---|---|---|---|
| Cl | Cl | =O | | 1 |
| OC₂H₅ | OC₂H₅ | =O | | 1 |
| Cl | Cl | | | 0 |
| O—φ | O—φ | =O | | 1 |
| O—φ | O—φ | | | 0 |

Example 8-continued

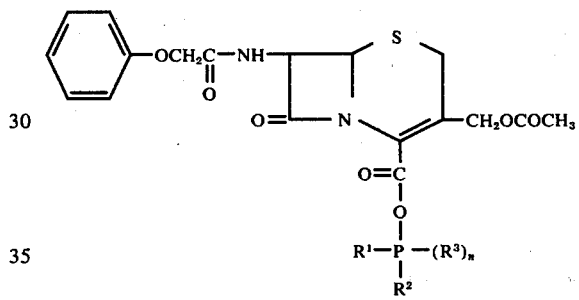

wherein R¹, R², R³, R¹+R² and n are defined as follows:

| R¹ | R² | R³ | R¹+R² | n |
|---|---|---|---|---|
| Br | Br | | | 0 |
| O—CH₂—φ | O—CH₂—φ | =O | | 0 |

The following tables are illustrative of other representative compounds that may be obtained in accordance with the processes described herein:

Table 1

| Starting Material | Phosphorylating Compound | Imino Halide Derivative of Formula IV | Imino Ether Derivative of Formula V | Hydrochloride Salt of 6-APA Derivative of Formula VI |
|---|---|---|---|---|
| 2-pentenyl penicillin | 2-chloro-1,3,2-dioxaphospholene | 6-[(1-bromo-3-hexenylidene)amino]penicillanic acid-1,3,2-dioxaphospholan-2-yl-ester | 6-[(1-phenoxy-3-hexenylidene)amino]penicillanic acid-1,3,2-dioxaphospholan-2-yl-ester | 6-aminopenicillanic acid-1,3,2-dioxa phospholan-2-yl-ester |
| n-heptyl penicillin | diethyl phosphorochloridate | 6-[(1-chlorooctylidene)amino]penicillanic acid monoanhydride with phosphoric acid diethyl ester | 6-[(1-ethoxyoctylidene)amino]penicillanic acid anhydride with phosphoric acid diethyl ester | 6-aminopenicillanic acid anhydride with phosphoric acid diethyl ester |
| 3,5-diphenyl-4-isoxazolyl penicillin | methyl phosphoro dichloridite | 6-[chloro(3,5-diphenyl-4-isoxazolylmethylene)amino]penicillanic acid monoanhydride with phosphorochloridous acid methyl ester | 6-[(α-ethoxy)-3,5-diphenyl-4-isoxazolylmethylene)amino]penicillanic acid monoanhydride with phosphorochloridous acid methyl ester | 6-aminopenicillanic acid monoanhydride with phosphorochloridous acid methyl ester |
| benzyl penicillin | diethyl phosphorochloridite | 6-[(α-bromophenethylidene)amino]penicillanic acid monoanhydride with phosphorus acid diethyl ester | 6-[(α-benzyloxyphenethylidene)amino]penicillanic acid monoanhydride with phosphorus acid diethyl ester | 6-aminopenicillanic acid monoanhydride with phosphorus acid diethyl ester |
| α-phenoxyethyl penicillin | phenyl phosphorodichloridate | 6-[(1-chloro-2-phenoxy propylidene)amino]penicillanic acid monoanhydride with phosphorochloridic acid phenyl ester | 6-[(1-methoxy-2-phenoxypropylidene)amino]penicillanic acid monoanhydride with phosphorochloridic acid phenyl ester | 6-aminopenicillanic acid monoanhydride with phosphorochloridic acid phenyl ester |

Table 1-continued

| Starting Material | Phosphorylating Compound | Imino Halide Derivative of Formula IV | Imino Ether Derivative of Formula V | Hydrochloride Salt of 6-APA Derivative of Formula VI |
|---|---|---|---|---|
| 2-ethoxy naphthyl penicillin | 2-chloro-1,3,2-dioxaphosphorinane | 6-[[chloro(2-ethoxynapthyl)methylene]amino]penicillanic acid-1,3,2-dioxaphosphorinan-2-yl ester | 6-[(ethoxy(2-ethoxy napthyl)methylene)amino] penicillanic acid-1,3,2-dioxaphosphorinan-2-yl ester | 6-aminopenicillanic acid-1,3,2-dioxaphosphorinan-2-yl ester |
| cephalothin | dibenzyl phosphorochloridate | 7-[[1-chloro-2-(2-thienyl)ethylidene]amino]cephalosporanic acid monoanhydride with phosphoric acid dibenzyl ester | 7-[(1-ethoxy-2-(2-thienyl)ethylidene)amino]cephalosporanic acid monoanhydride with phosphoric acid dibenzyl ester | 7-aminocephalosporanic acid monoanhydride with phosphoric acid dibenzyl ester |

Table 2

| Hydrochloride Salt of 6-APA or 7-ACA Derivative | Acylating Agent | Acylated Penicillin or Cephalosporin | Final Penicillin or Cephalosporin |
|---|---|---|---|
| 6-aminopenicillanic acid, 1,3,2-dioxaphospholan-2-yl ester | benzene sulfonyl chloride | 6-(benzenesulfonamido)penicillanic acid, 1,3,2-dioxaphospholan-2-yl ester | 6-(benzenesulfonamido)penicillanic acid |
| 6-aminopenicillanic acid monoanhydride with phosphoric acid diethyl ester | N-carboxyanhydride of 2-amino-2-phenoxy-2-indane carboxylic acid | 6-(2-amino-2-phenoxy-2-indane carboxamido)penicillanic acid monoanhydride with phosphoric acid diethyl ester | 6-(2-amino-3-phenoxy-2-indanecarboxamido)penicillanic acid |
| 6-aminopenicillanic acid monoanhydride with phosphorochloridous acid methyl ester | furane-2-carboxylic acid chloride | 6-(2-furanecarboxamido)penicillanic acid monoanhydride with phosphorochloridous acid methyl ester | 6-(2-furanecarboxamido)penicillanic acid |
| 6-aminopenicillanic acid monoanhydride with phosphorus acid diethyl ester | N-carboxyanhydride of 2-amino-2-phenoxy-2-indane carboxylic acid | 6-(2-amino-3-phenoxy-2-indane carboxamido)penicillanic acid monoanhydride with phosphorus acid diethyl ester | 6-(2-amino-3-phenoxy-2-indane carboxamido)penicillanic acid |
| 6-aminopenicillanic acid monoanhydride with phosphorochloridic acid phenyl ester | N-carboxyanhydride of 1-aminocyclopentane carboxylic acid | 6-(1-aminocyclopentanecarboxamido)penicillanic acid monoanhydride with phosphorochloridic acid phenyl ester | 6-(1-aminocyclopentanecarboxamido) penicillanic acid |
| 6-aminopenicillanic acid-1,3,2-dioxaphospholan-2-yl ester | D(-)phenyl glycyl chloride hydrochloride | 6-(α-aminophenylacetamido)penicillanic acid-1,3,2-dioxaphospholan-2-yl ester | 6-(α-aminophenylacetamido)penicillanic acid |
| 7-aminocephalosporanic acid monoanhydride with phosphoric acid dibenzyl ester | N-carboxyanhydride of 1-aminocyclohexane carboxylic acid | 7-(1-aminocyclohexanecarboxamido)cephalosporanic acid monoanhydride with phosphoric acid dibenzyl ester | 7-(1-aminocyclohexaneacetamide) cephalosporanic acid |

What is claimed is:

1. A hydrohalide salt of the formula:

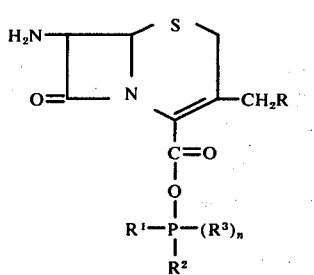

wherein:
R is selected from the class consisting of hydrogen, (lower) alkanoyloxy containing 2 to 8 carbon atoms, phenoxy, naphthoxy and a quaternary ammonium radical; $R^1$ and $R^2$ are selected from the class consisting of (lower)alkoxy, (lower)alkylthio, phenyl, naphthyl, phenoxy, naphthoxy, halo, phenylthio, phenyl(lower)alkyl, phenyl(lower)alkylthio, phenyl(lower)alkoxy, (lower)alkyl, halo(lower)alkyloxy, a radical of the formula

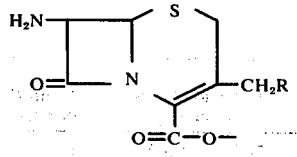

$R^1$ and $R^2$ when joined together form with the phosphorus atom the ring

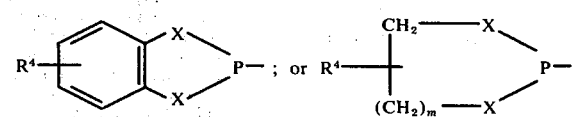

$R^3$ is the oxygen atom which when present is linked by a double bond to the phosphorus atom; X is selected from the class consisting of oxygen, sulfur and methylene; $R^4$ is selected from the class consisting of hydrogen and (lower)alkyl; n is an integer from 0 to 1; m is an integer from 1 to 6.

2. The hydrohalide salt of the formula:

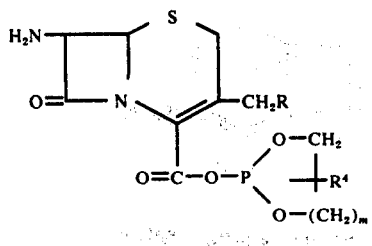

wherein:
R⁴ is selected from the class consisting of hydrogen and lower alkyl; and m is an integer from 1 to 6.

3. A compound according to claim 2 which is the hydrochloride salt of 7-aminocephalosporanic acid, 1,3,2-dioxaphospholan-2-yl ester.

4. A compound according to claim 2 which is the hydrochloride salt of 7-aminodesacetoxycephalosporanic acid, 1,3,2-dioxaphospholan-2-yl ester.

5. A process for preparing a semi-synthetic cephalosporin which comprises:

a. reacting a cephalosporin compound of the formula

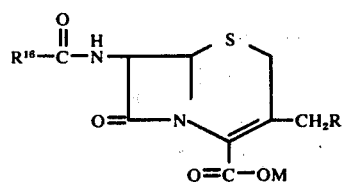

with a phosphorylating agent of the formula

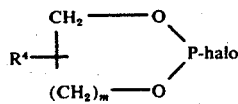

to produce a compound of the formula

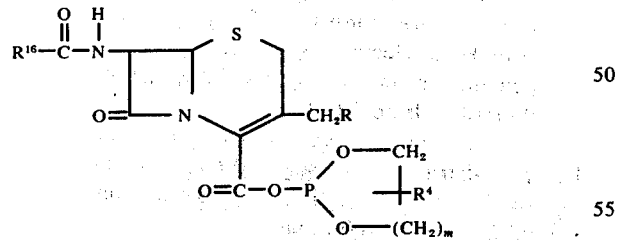

said reaction being carried out under anhydrous conditions in the presence of an inert non-hydroxylic organic solvent and a tertiary amine at a temperature in the range of about −40° C to about +10° C, the molar ratio of said cephalosporin compound to said phosphorylating agent being about 0.5:1 to about 3:1;

b. reacting said compound obtained in step (a) with an acid chloride in the presence of a tertiary amine at a temperature between about −10° C and −65° C to produce an imino chloride compound of the formula

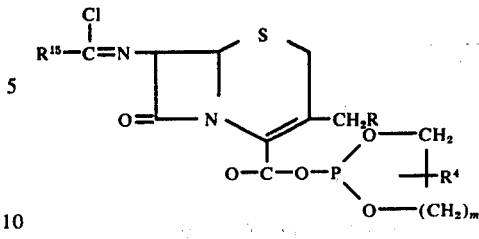

c. reacting said imino chloride with an alcohol at a temperature below about −10° C to produce an imino ether of the formula

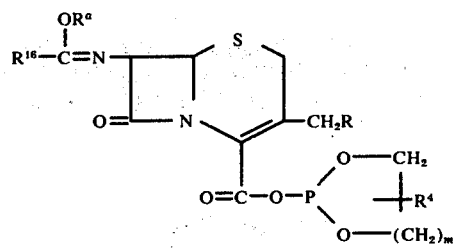

d. reacting said imino ether with water at a temperature below about −20° C and treating the resulting compound with a reactive derivative of an organic carboxylic acid in the presence of a tertiary amine at a temperature between about 0° C and −60° C to produce a compound of the formula

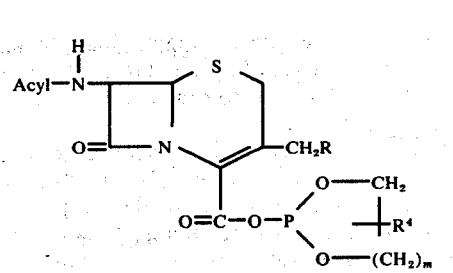

e. and hydrolyzing the resulting acylated product to remove the carboxyl protective group and obtain a semi-synthetic cephalosporin;

wherein:
M is selected from the class consisting of hydrogen, an alkali metal and a tertiary amine; R is selected from the class consisting of hydrogen (lower)alkanoyloxy containing 2 to 8 carbon atoms, phenoxy, naphthoxy and a quaternary ammonium radical; R¹⁶ is selected from the class consisting of 2-thienylmethyl and 4-amino-4-carboxy-n-butyl; R⁴ is selected from the class consisting of hydrogen and lower alkyl; Rᵃ is selected from the class consisting of lower alkyl, phenyl(lower)alkyl, cycloalkyl of 4 through 8 carbon atoms, phenoxy(lower)alkyl, (lower)alkoxy, (lower)alkyl; and m is an integer from 1 to 6.

6. A process for preparing a semi-synthetic cephalosporin which comprises:

a. reacting a compound of the formula:

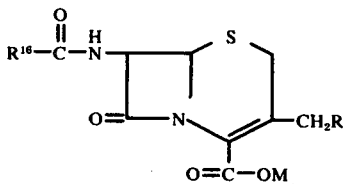

with a phosphorylating agent of the formula

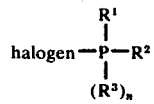

in the presence of an acid binding agent and an inert, non-hydroxylic organic solvent at a temperature between about −40° C and about +10° C to obtain a compound of the formula:

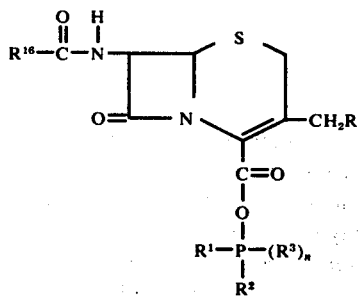

b. reacting an acid halide with a compound obtained in step (a) in the presence of an acid binding agent at a temperature below 0° C to produce the corresponding imino halide;

c. reacting said imino halide compound with a alcohol at a temperature below about −10° C to convert said imino halide compound to the hydrohalide salt of the corresponding imino ether compound; d. converting said imino ether compound by hydrolysis at a temperature below about −20° C to the hydrohalide salt of a compound of the formula

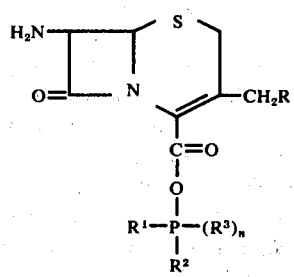

e. reacting a compound formed in step (d) with an acylating agent selected from an organic carboxylic acid and a functional reactive derivative of such acid in the presence of an acid binding agent to obtain acylation of the amino group; and f. treating said acylated compound with sufficient water to obtain a compound of the following formula:

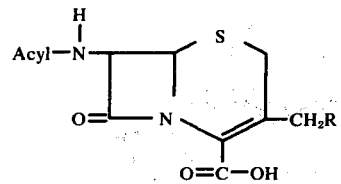

and the corresponding acid addition salt where a free amino group is present on the acyl radical, wherein:

M is selected from the class consisting of hydrogen, an alkali metal and a tertiary amine; R is selected from the class consisting of hydrogen, (lower)alkanoyloxy containing 2 to 8 carbon atoms, phenoxy, naphthoxy and a quaternary ammonium radical; $R^{16}$ is a substituent selected from those contained in a natural and semi-synthetic cephalosporin; $R^1$ and $R^2$ are selected from the class consisting of (lower)alkoxy, (lower)alkylthio, phenyl, naphthyl; phenoxy, naphthoxy, phenylthio, phenyl(lower)alkyl, phenyl(lower)alkylthio, halogen, lower alkyl, halo(lower)alkyl, halo(lower)alkyl, halo(lower)alkyloxy, a radical of the formula

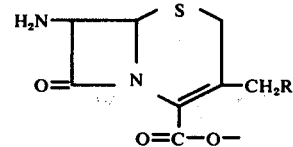

$R^1$ and $R^2$ when joined together form with the phosphorus atom the ring

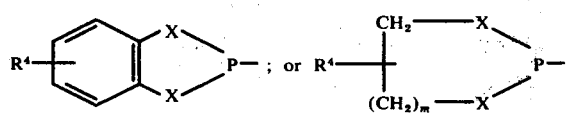

$R^3$ is the oxygen atom which when present is linked by a double bond to the phosphorus atom; X is selected from the class consisting of oxygen, sulfur and methylene; $R^4$ is selected from the class consisting of hydrogen and (lower)alkyl; $n$ is an integer from 0 to 1; $m$ is an integer from 1 to 6.

7. A process according to claim 6 wherein said phosphorylating agent is selected from the class consisting of 2-chloro-1,3,2-dioxaphospholane and 2-chloro-1,3,2-dioxaphosphorinane.

8. A process according to claim 7 wherein said acylating agent is selected from the class consisting of D(−)phenylglycyl chloride hydrochloride and 2-thienylacetic acid chloride.

9. A process according to claim 6 wherein said phosphorylating agent is phosphorus trichloride.

10. A process according to claim 6 wherein $R^{16}$ is selected from the class consisting of 2-thienylmethyl and 4-amino-4-carboxy-n-butyl.

11. A process according to claim 6 wherein said phosphorylating agent is

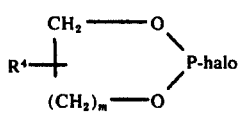

12. A process according to claim 6 wherein $R^{16}$ is a substituent contained in a natural cephalosporin.

13. A process which comprises reacting a hydrohalide salt of 7-aminocephalosporanic acid, 1,3,2-dioxaphospholan-2-yl-ester with phenylglycylchloride, hydrochloride in the presence of a tertiary amine and a non-hydroxylic organic solvent at a temperature of about 0° to −60° C., and treating the resulting product with water to produce the hydrochloride salt 7-(α-aminophenylacetamido)cephalosporanic acid.

14. A process for preparing a semi-synthetic cephalosporin which comprises reacting a hydrohalide salt of a compound of the formula:

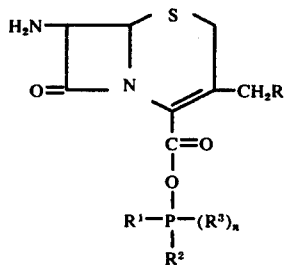

with an acylating agent which is an organic carboxylic acid or a reactive derivative thereof in the presence of an acid binding agent and thereafter treating the resulting product with water to produce an acid addition salt of a compound of the formula

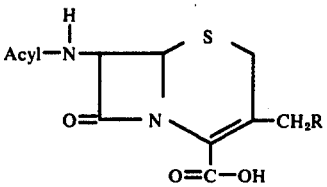

wherein:
R is selected from the class consisting of hydrogen (lower)-alkanoyloxy containing 2 to 8 carbon atoms, phenoxy, naphthoxy and a quaternary ammonium radical; $R^1$ and $R^2$ are selected from the class consisting of halogen, (lower)alkoxy, (lower)alkylthio, phenyl, naphthyl, phenoxy, naphthoxy, phenylthio, phenyl(lower)alkyl, phenyl(lower)alkylthio, phenyl(lower)alkyloxy, (lower)alkyl, halo(lower)alkyloxy, a radical of the formula

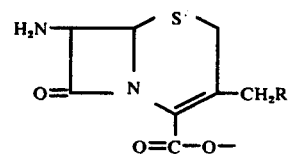

$R^1$ and $R^2$ may be joined together to form with the phosphorus atom the ring

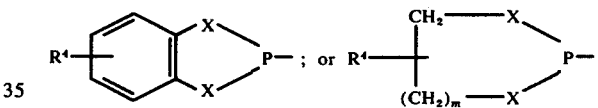

$R^3$ is the oxygen atom which when present is linked by a double bond to the phosphorus atom; $R^4$ is selected from the class consisting of hydrogen and (lower)alkyl; X is selected from the class consisting of oxygen, sulfur and methylene; $n$ is an integer from 0 to 1; $m$ is an integer from 1 to 6.

* * * * *